US00PP25092P3

(12) United States Plant Patent
Zaiger et al.

(10) Patent No.: US PP25,092 P3
(45) Date of Patent: Nov. 25, 2014

(54) NECTARINE TREE NAMED 'POLAR SWEET'

(50) Latin Name: ***Prunus persica* var. *nucipersica***
Varietal Denomination: Polar Sweet

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 13/986,257

(22) Filed: Apr. 17, 2013

(65) Prior Publication Data

US 2014/0317795 P1 Oct. 23, 2014

(51) Int. Cl.
*A01H 5/08* (2006.01)

(52) U.S. Cl.
USPC ..... Plt./188

(58) Field of Classification Search
CPC ..... A01H 5/08
USPC ..... Plt./188
See application file for complete search history.

*Primary Examiner* — June Hwu
*Assistant Examiner* — Keith Robinson

(57) ABSTRACT

A new and distinct variety of nectarine tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright tree growth.
2. Regular and productive bearer of large size fruit.
3. Fruit having a high degree of attractive red skin color.
4. Fruit with mild, sweet, sub-acid flavor and excellent eating quality.
5. Firm, white flesh fruit with good shipping quality.

1 Drawing Sheet

Botanical designation: *Prunus persica* var. *nucipersica*.
Variety denomination: 'Polar Sweet'.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of nectarine tree was originated and asexually reproduced by us in our experimental orchard located near Modesto, Stanislaus County, Calif.

2. Prior Varieties

Among the existing varieties of nectarine trees, which are known to us, and mentioned herein, 'Arctic Queen' Nectarine (U.S. Plant Pat. No. 8,094) and our proprietary non-patented nectarine selections '215LV498', '120LH142' and '381LN4'.

STATEMENT REGARDING FEDERALLY SPONSORED RESEARCH AND DEVELOPMENT

Not applicable.

ORIGIN OF THE VARIETY

The new variety of nectarine tree (*Prunus persica* var. *nucipersica*) was originated by us in our experimental orchard located near Modesto, Calif. as an open pollinated seedling selection from seed collected from our proprietary non-patented nectarine selection with the field identification number '215LV498'. The proprietary seed parent '215LV498' originated as a second generation seedling from the cross of our proprietary non-patented nectarine seedling selections '120LH142' and '381LN4'. We planted and maintained a large group of these open pollinated seedlings on their own root system. Under close and careful evaluation we recognized the desirable tree and fruit characteristics of the present variety and selected it in 2006 for asexual propagation and commercialization.

ASEXUAL REPRODUCTION OF THE VARIETY

Asexual reproduction of the new and distinct variety of nectarine tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of nectarine tree (*Prunus persica* var. *nucipersica*) is of large size, vigorous, upright growth and a productive and regular bearer of large size, white flesh, clingstone fruit. The fruit is further characterized by having mild, sweet, sub-acid flavor with excellent eating quality. In comparison to its immediate seed parent '215LV498' nectarine (non-patented) the fruit of the new variety is larger in size and is approximately 5 days later in maturity. In comparison to the commercial variety 'Arctic Queen' Nectarine (U.S.

Plant Pat. No. 8,094) the fruit of the new variety is clingstone instead of freestone and is approximately 8 days later in maturity.

DESCRIPTION OF THE PHOTOGRAPH

The accompanying color photographic illustration shows typical specimens of the foliage and fruit of the present new nectarine variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 5 year old tree and the colors are as nearly true as is reasonably possible in a color representation of this type.

DESCRIPTION OF THE VARIETY

The following is a detailed botanical description of the new variety of nectarine tree, its flowers, foliage and fruit, as based on observations of 5 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters in height the first growing season. Varies with soil type, fertility of soil and climatic conditions.

*Form*.—Upright, usually pruned to vase shape.

*Branching habit*.—Upright, crotch angle approximately 35°, increases with heavy crop load.

*Productivity*.—Productive, thinning and spacing of fruit necessary for desired market size. Fruit set varies with climatic conditions during bloom time.

*Bearer*.—Regular, adequate fruit set 3 consecutive years. No alternate bearing observed.

*Fertility*.—Self-fertile.

*Density*.—Medium dense, usually pruned to vase shape to allow more sunlight to center of tree to enhance fruit color and health of fruit wood.

*Hardiness*.—Hardy in all stone fruit growing areas of California. Tree grown in USDA Hardiness Zone 9. Winter chilling requirement approximately 800 hours at or below 45° F.

Trunk:

*Size*.—Medium to large. Average circumference 39.1 cm at 28.0 cm above ground on a 5 year old tree.

*Stocky*.—Medium stocky.

*Texture*.—Medium shaggy, roughness increases with age.

*Color*.—Varies from 2.5Y 3/2 to 5Y 3/2.

Branches:

*Size*.—Medium. Average circumference 10.9 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 27 in a 25.8 square cm section. Average length 3.6 mm. Average width 1.4 mm. Color varies from 10YR 4/6 to 7.5YR 4/8.

*Color*.—New growth varies from 5GY 7/6 to 7.5R 4/6 where exposed to the sun. Mature growth varies from 7.5YR 3/4 to 7.5YR 2/4, varies with age of growth.

Leaves:

*Size*.—Large. Average length 131.9 mm. Average width 32.7 mm.

*Form*.—Lanceolate.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 11.4 mm. Average width 1.4 mm. Longitudinally grooved. Surface glabrous. Color varies from 5GY 4/6 to 5GY 4/8.

*Glands*.—Type — reniform. Size — medium. Average length 1.3 mm. Average diameter 0.8 mm. Number varies from 2 to 4, average number 3. Located primarily on the base of the leaf blade and the upper portion of the petiole. Color varies from 2.5GY 6/6 to 5GY 5/6.

*Stipules*.—Average number 2. Average length 11.0 mm. Edges — pectinate. Color — 5GY 5/8.

*Color*.—Upper surface varies from 5GY 3/6 to 7.5GY 3/6. Lower surface varies from 5GY 5/4 to 5GY 4/6. Midvein color varies from 2.5GY 8/4 to. 5GY 9/4.

Flower buds:

*Size*.—Large. Average length 18.2 mm. Average diameter 8.6 mm.

*Hardiness*.—Hardy with respect to California winters.

*Form*.—Elongated.

*Pedicel*.—Average length 4.0 mm. Average width 1.2 mm. Color varies from 2.5GY 7/8 to 5GY 7/6. Surface glabrous.

*Density*.—Medium.

*Color*.—Varies from 5RP 6/12 to 7.5RP 6/10.

Flowers:

*Blooming period*.—Date of First Bloom Feb. 23, 2012. Date of Petal Fall Mar. 5, 2012, varies slightly with climatic conditions.

*Size*.—Large, showy. Average height 21.0 mm. Average diameter 42.2 mm.

*Petals*.—Normally 5, alternately arranged to sepals. Size — large. Average length 22.1 mm. Average width 16.5 mm. Form — elliptical. Arrangement — free. Margin — sinuate. Color varies from 5RP 8/4 to 7.5RP 8/4, fades with age of flower. Both surfaces glabrous.

*Sepals*.—Normally 5, alternately arranged to petals. Size — large. Average length 6.7 mm. Average width 5.4 mm. Shape — ovate. Margin — entire. Color — upper surface varies from 5GY 5/8 to 7.5R 2/6. Lower surface varies from 7.5R 2/4 to 10R 2/6. Surface — upper surface glabrous, lower surface pubescent.

*Stamens*.—Average number per flower 42. Average filament length 15.6 mm. On average, the stamens are even with the height of the petals. Filament color varies from N 9.5/(white) to 5RP 5/10. Anther color varies from 7.5R 3/10 to 7.5R 3/12.

*Pollen*.—Self fertile. Color varies from 2.5Y 7/10 to 5Y 7/10.

*Pistil*.—Number — normally one. Surface glabrous. Average length 16.8 mm. Position of stigma an average of 3.3 mm below anthers. Color varies from 10Y 8/6 to 10Y 7/6.

*Fragrance*.—Heavy.

*Color*.—Varies from 5RP 8/4 to 5RP 7/6.

*Number flowers per flower bud*.—Normally one.

*Pedicel*.—Average length 4.3 mm. Average width 1.7 mm. Color varies from 2.5GY 7/6 to 2.5GY 6/6. Surface glabrous.

Fruit:

*Maturity when described*.—Firm ripe.

*Date of first picking*.—Aug. 2, 2012.

*Date of last picking*.—Aug. 10, 2012, varies slightly with climatic conditions.

*Size*.—Large. Average diameter axially 69.8 mm. Average transversely in suture plane 74.9 mm. Average weight 218.7 grams, varies slightly with fertility of soil, amount of thinning and climatic conditions.

*Form*.—Globose.

*Suture*.—Nearly smooth, extends from base to apex.

*Ventral surface*.—Smooth to slightly lipped.

*Apex*.—Rounded to slight tip.

*Base*.—Retuse.

*Stem cavity*.—Rounded to slightly elongated in the suture plane. Average depth 7.5 mm. Average diameter 7.2 mm.

Stem:

*Size*.—Small. Average length 11.6 mm. Average diameter 2.9 mm.

*Color*.—Varies from 2.5GY 6/6 to 5GY 6/6.

Flesh:

*Ripens*.—Evenly.

*Texture*.—Firm, meaty.

*Fibers*.—Few, small, tender.

*Firmness*.—Good, comparable to other commercial varieties.

*Aroma*.—Moderate.

*Amydgalin*.—Undetected.

*Eating quality*.—Excellent.

*Flavor*.—Excellent, mild, sweet, sub-acid.

*Juice*.—Moderate amount, enhances flavor.

*Brix*.—Average Brix 14.0°, varies slightly with amount of fruit per tree and climatic conditions.

*Pit cavity*.—Average length 42.8 mm. Average width 28.6 mm. Average depth 12.0 mm. Color varies from 10Y 9/2 to 7.5R 2/6.

*Color*.—Varies from 7.5Y 9/2 to 10Y 9/2.

Skin:

*Thickness*.—Medium.

*Surface*.—Smooth.

*Pubescence*.—Wanting.

*Tendency to crack*.—None.

*Color*.—Ground color varies from 5Y 9/4 to 5Y 9/6. Overspread with 7.5R 3/10 to 7.5R 2/6.

*Tenacity*.—Tenacious to flesh.

*Astringency*.—Undetected.

Stone:

*Type*.—Clingstone. Adherence to flesh-present, strong.

*Size*.—Large. Average length 41.8 mm. Average width 27.5 mm. Average thickness 22.1 mm.

*Form*.—Obovoid.

*Base*.—Flat.

*Apex*.—Pointed. Average length 1.6 mm.

*Surface*.—Pitted throughout, pits vary from round to elongated.

*Sides*.—Unequal, side extending further from the suture plane.

*Ridges*.—Relatively smooth, narrow ridges extending from base toward apex.

*Tendency to split*.—None.

*Color*.—Varies from 5R 2/2 to 5R 2/4 when dry.

Kernel:

*Size*.—Large. Average length 20.1 mm. Average width 11.9 mm. Average depth 6.8 mm.

*Form*.—Ovoid.

*Viability*.—Viable, complete embryo development.

*Skin color*.—Varies from 5Y 9/4 to 7.5Y 9/4.

Use:

*Dessert*.—Market — local and long distance.

Keeping quality: Good, held firm in cold storage at 38° to 42° F. for weeks without internal breakdown of flesh or appreciable loss of flavor.

Shipping quality: Good, minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of nectarine tree, substantially as illustrated and described.

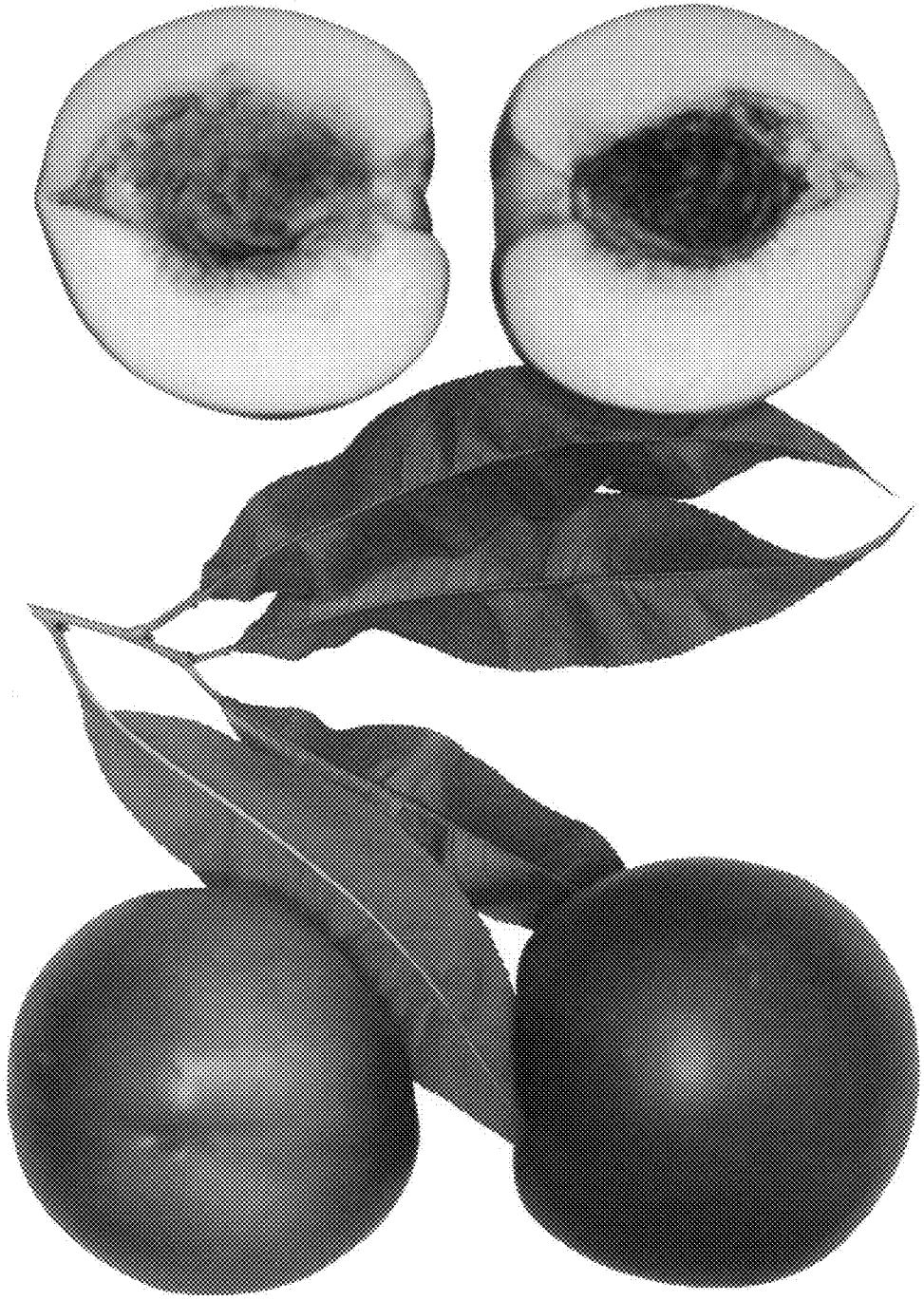

* * * * *